| United States Patent [19]
Blytas et al.

[11] Patent Number: 4,665,240
[45] Date of Patent: May 12, 1987

[54] PROCESS FOR THE PRODUCTION OF DICHLOROHYDRIN

[75] Inventors: George C. Blytas; Stephen A. Shain, both of Houston, Tex.

[73] Assignee: Shell Oil Company, Houston, Tex.

[21] Appl. No.: 866,803

[22] Filed: May 27, 1986

[51] Int. Cl.$^4$ ..................... C07C 29/66; C07C 31/40
[52] U.S. Cl. ..................................... 568/847; 210/652
[58] Field of Search ......................... 568/847; 210/652

[56] References Cited
FOREIGN PATENT DOCUMENTS 921413 3/1963 United Kingdom ................ 568/847
931211 7/1963 United Kingdom ................ 568/847

Primary Examiner—Howard T. Mars
Attorney, Agent, or Firm—Ronald R. Reper

[57] ABSTRACT

A continuous process for the production of dichlorohydrin by the reaction of chlorine, water and allyl chloride, having reduced water consumption wherein the dichlorohydrin formed is extracted into an inert organic solvent and the remaining aqueous reaction product is subjected to reverse osmosis, and at least a portion of the resulting permeate is recycled to the reaction.

7 Claims, 1 Drawing Figure

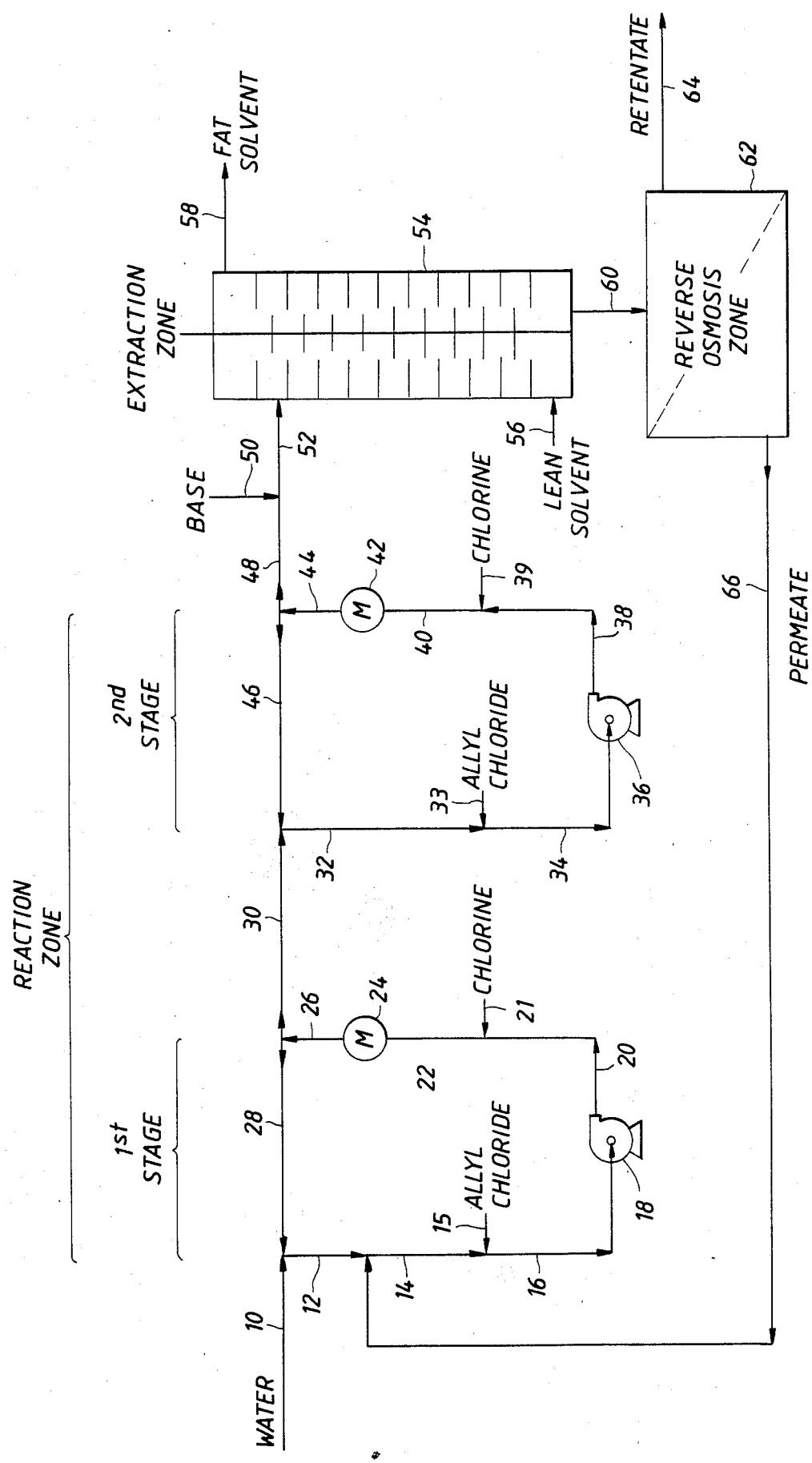

PROCESS FOR THE PRODUCTION OF DICHLOROHYDRIN

BACKGROUND OF THE INVENTION

It is known to prepare dichlorohydrin by reacting in a reaction zone allyl chloride, water and chlorine in dilute aqueous phase, see e.g. U.S. Pat. Nos. 2,714,121 and 2,714,123, incorporated herein by reference. The term "dichlorohydrin" herein designates the isomers 2,3 dichloro-1-propanol and 1,3 dichloro-1-propanol. The reaction zone effluent may be worked up in various ways to recover the dichlorohydrin therefrom, or may be processed further in an integrated process to convert the dichlorohydrin to derivatives such as epichlorohydrin and/or glycerine.

It is known e.g., from Belgian Pat. Nos. 614,890 and 614,891 that dichlorohydrin may be extracted from aqueous solution with organic solvents such as phosphate esters of aliphatic monohydric alcohols containing more than four carbon atoms, aryl phosphates, and liquid aliphatic alcohols and liquid ketones having 8 to 18 carbon atoms per molecule.

One disadvantage of the known processes is that substantial amounts of water are used in the reaction zone of the process to reduce formation of undesired by-products, which by-products reduce the overall efficiency of the process and may complicate purification procedures of the desired product. Such conventional processes result in an aqueous effluent stream which contains minor amounts of organic impurities diluted in a substantial amount of water. Such effluent requires energy intensive treatment to reduce the amount of organic materials to levels acceptable to be passed to receiving bodies of water such as rivers, lakes and the like. Considerable savings could be effected if the amount of water to be treated could be significantly reduced.

SUMMARY OF THE INVENTION

According to the invention, there is provided in a continuous process for the production of an organic solvent solution of dichlorohydrin, the method for reducing the quantity of fresh water used in the reaction, which method comprises:
(a) reacting allyl chloride, water and chlorine in a reaction zone to form an aqueous solution of dichlorohydrin,
(b) extracting in an extraction zone the reaction zone effluent with a water-immiscible inert organic solvent for the dichlorohydrin to obtain a dichlorohydrin-enriched solvent and an aqueous phase,
(c) passing said dichlorohydrin-enriched solvent from said extraction zone,
(d) passing said aqueous phase from the extraction zone as feed to a reverse osmosis zone,
(e) subjecting said aqueous phase to reverse osmosis to obtain: (1) a retentate stream having chloride content higher than said aqueous phase, and (2) a permeate stream having chloride content lower than said aqueous phase,
(f) withdrawing said retentate stream, and
(g) recycling at least part of said permeate stream from step (e) to the reaction zone of step (a).

THE DRAWING

The drawing depicts a schematic flow diagram of a preferred embodiment of the invention.

DESCRIPTION OF PREFERRED EMBODIMENTS

In the principal reaction, allyl chloride is converted to a mixture of the two isomers of glycerol dichlorohydrin by reaction with hypochlorous acid, HClO, which is readily formed when chlorine is dissolved in water. The chlorohydrination reaction takes place readily at temperatures in the range from about 15° to about 55° C. Decreased temperature rapidly increases the amount of dissolved chlorine as well as the concentration of the hypochlorous acid. For maximum dichlorohydrin yield it is necessary to run the reaction at low concentrations of chloride ion and of dichlorohydrin, i.e., with high water dilution. The presence of excess allyl chloride and of chloride ions during the reaction typically results in the formation of undesired by-products e.g., trichloropropane and tetrachloropropylether.

Inert organic solvents suitably employed to effectively remove glycerol dichlorohydrins from aqueous solution include liquid organic esters, especially phosphate esters, which are immiscible with water. Preferred are esters containing from about 4 to about 28 carbon atoms, especially from about 6 to about 18 carbon atoms. Representative compounds are n-butyl acetate, tributylphosphate, tri-(2 ethylhexyl)phosphate, butyl dioctylphosphate, tri-n-octylphosphate, trihexylphosphate, tridecylphosphate and trioctadecylphosphate. Exemplary aryl phosphates include tricresyl phosphate, dicresyl phosphate, diphenyl cresyl phosphate, triphenyl phosphate, 2-ethylhexyl-diphenyl phosphate, o-chlorophenyldiphenyl phosphate, bis-(p-tert-butylphenyl) phenyl phosphate and didecylphenyl phosphate. The phosphate esters, if desired, may be combined with one or more of various liquid hydrocarbon thinners to result in a more desirable density or viscosity of the solvent phase. The thinner should, of course, be inert to the reaction components and insoluble in the aqueous phase. Exemplary materials which may be used as solvents or as thinners include hexane, benzene, heptane, n-octane, methylcyclohexane, petroleum naphthas, kerosene and the like.

Additional solvents include liquid aliphatic alcohols and ketones containing from about 4 to about 18 carbon atoms especially from about 5 to about 18 carbon atoms. Representative compounds include methyl isobutyl ketone, n-hexanol isodecanol, isobutyl heptyl ketone, 5-ethyl-2-nonanol, 7-ethyl-2-methyl-4-undecanol, heptadecanol, oleyl alcohol, linolyl alcohol, 1-nonanol, 2-nonanol, diisobutylcarbinol, diisobutyl ketone, 2-nonanone, 5-nonanone, lauryl alcohol, 1-hendecanol, 3-hendecanone, diisoamyl ketone and 4-decanone. Although chloro- and nitro-substituted derivatives of said compounds may also be suitable, preferred among those compounds as solvent is a saturated aliphatic alcohol or ketone.

Further solvents include ethers such as ethyl ether and isopropyl ether and chlorinated hydrocarbons such as methylene chloride, chloroform, carbon tetrachloride and trichloropropane. Preferred among those compounds as solvent is a saturated aliphatic ether or chlorinated hydrocarbon containing up to about 9 preferably up to 8 carbon atoms.

The extraction is carried out employing conventional extraction techniques, wherein the dichlorohydrin is extracted into the solvent. The solvent is then removed from the remaining aqueous phase, following which the solvent may be distilled off from the dichlorohydrin and recycled to the extraction zone.

The reaction zone effluent typically has a low pH e.g. about 0.3 to 1.0, resulting from the formation of hydrogen chloride as by-product in the formation of the dichlorohydrin. It is preferred that the effluent prior to extraction be partially neutralized to a pH in the range from about 1.5 to about 7.0 and preferably from about 3.0 to 6.5 by the addition of a basic compound such as an alkali metal hydroxide. This may facilitate both the separation of the solutions in the extraction step and subsequent reverse osmosis step of the aqueous raffinate. An additional advantage is that the less corrosive nature of the effluent will permit a wider choice of less expensive materials of construction in the extraction zone.

After the extraction, the aqueous phase is fed to a reverse osmosis zone comprising one or more reverse osmosis units. Said aqueous feed is subjected to reverse osmosis to form an ionic retentate stream having a higher content of organic and inorganic chlorides than said feed, and a permeate stream of relatively pure water, i.e. substantially depleted in both organic and inorganic chlorides. The retentate stream, which has considerably reduced volume compared to the reverse osmosis zone feed volume, is removed from the reverse osmosis zone for further treatment and/or disposal. Preferably said retentate stream is subjected to steam stripping to recover as overhead any entrained solvent and/or dichlorohydrin that may be present. At least a major portion of the permeate stream is recycled to the reaction zone. The permeate stream after the reverse osmosis step is substantially depleted in both undesirable ions and organic compounds and is recycled to the reaction zone, thereby reducing by a like amount the quantity of fresh i.e., unused water required for high yield production of the dichlorohydrin. It is preferred that at least about 50% by volume of the permeate, more preferably at least about 75% by volume of the permeate, and most preferably that all of the permeate is recycled to the reaction zone. The retentate stream from the reverse osmosis step has considerably reduced volume and accordingly requires substantially less energy for subsequent treatment or disposal.

An embodiment of the invention will now be described with reference to the accompanying drawing which shows diagrammatically a preferred assemblage adapted to the continuous manufacture of dichlorohydrin. Although the reaction stages in this embodiment are shown to be circulating loop reactors, as will be obvious to those skilled in the art the reaction stages suitably can be stirred reactors such as e.g., vane disc turbine dispersers, sprayed towers or other equipment known to be suitable for chlorohydrin reactions.

Referring to the drawing, a fresh water stream is continuously introduced through conduit 10 into a first stage reaction loop comprising conduits 12, 14, 16, pump 18, conduits 20, 22, motor driven mixer 24 and conduits 26 and 28. Allyl chloride is continuously fed into the water stream through conduit 15, while chlorine in an amount substantially equimolar with respect to the allyl chloride is fed to the reaction loop through conduit 21. The relatively dilute reaction mixture is circulated through the loop and a portion of the mixture after passing through pump 18 and mixer 24 is continuously diverted via conduit 30 to the second stage, a like reaction loop comprising conduits 32 and 34, pump 36 conduits 38 and 40, mixer 42, and conduits 44 and 46. The diverted portion of the first stage reaction effluent forms the make-up liquid added to the reaction mixture in the second stage where further quantities of allyl chloride and chlorine are added via conduits 33 and 39 respectively. A portion of the stream in line 44, which is more concentrated than that in line 26 is continuously discharged as product.

Additional reaction stages, for example three, four, five or more, could be employed, as desired, serving to further decrease the formation of by-products in the aqueous phase. It is preferred that substantially all of the water be added to the first in the series of reaction stages since this represents the most efficient method of operation.

The final concentration of the aqueous reaction mixture may vary within relatively wide limits. Preferably the total of from about 0.02 to 0.1 volume of allyl chloride (and a substantially equimolar quantity of chlorine) is added for each volume of water supplied to the system. The reaction may be conducted within a wide temperature range and under atmospheric, subatmospheric or superatmospheric pressures. In general, reaction temperatures between 15 and 60° C., preferably between about 25° and 55° C. can be employed. The reaction between allyl chloride and hypochlorous acid (formed in-situ by the reaction of chlorine and water) proceeds rapidly and is normally complete within one or two seconds, however, total residence times in the reaction zone (total of all stages) of from 1 to about 10 minutes may be employed. The total residence time is determined by dividing the total volume of the system by the rate of reaction product draw off per minute.

A basic material is added to the reaction zone effluent via conduit 50 to partially neutralize the effluent to a pH in the range from about 5 to about 6.5. Although in theory any basic material may be added, it is found that poorly soluble materials such as lime and calcium carbonate tend to promote the formation of emulsions in the subsequent extraction step (A). Accordingly, it is preferred that the basic material be a solution of soluble hydroxide or carbonate of a Group I metal such as lithium, potassium or sodium. Of these, sodium hydroxide is preferred owing to its lower cost and ready availability.

The reaction zone effluent after adjustment of the pH is passed via conduit 52 to extraction zone 54 which may be any conventional liquid-liquid extractor such as an agitated vessel, jet mixer, or perforated plate tower, but preferably is a rotating disc contactor, as shown. Although cocurrent extraction may be suitable, countercurrent extraction is preferred. As illustrated in the drawing, the reaction zone effluent enters near the top of extraction zone 50 and the down-flowing aqueous phase contacts upflowing inert organic solvent which is less dense than water such as isopropyl ether entering the lower part of the extraction zone via conduit 56. As will be understood by those skilled in the art, when employing an inert organic solvent having a density greater than the reaction mixture e.g., carbon tetrachloride, the more dense solvent would be introduced near the top of the extraction zone, and the reaction effluent would enter near the bottom of the extraction zone. The rotating center shaft of the contactor shown is equipped with disc baffles to facilitate extraction of the dichlorohydrin from the downflowing reaction zone aqueous phase into the upflowing inert organic solvent. Generally, substantially complete extraction of the dichlorohydrin present can be achieved if the solvent is contacted with the aqueous phase in a solvent to aqueous phase weight ratio of from about 1:1 to about 1:20, with weight ratio of about 1:2 to 1:10 being preferred. The dichlorohydrin-fat solvent then passes from the extraction zone 54 via conduit 58 for separation of the solvent from the dichlorohydrin (not shown) and is recycled to the extraction zone via conduit 56, with or without intermediate storage, as desired.

As will be apparent to those skilled in the art, the temperature of the extraction step can be suitably controlled by adjusting the temperature of the solvent added. Further, in order to compensate for minor solvent losses through the process, a small amount of solvent maybe added along with the recycle solvent (not shown) to maintain the desired ratio of solvent to reaction zone effluent in the extracting step of the process.

The dichlorohydrin-depleted aqueous phase is removed from the bottom of extraction zone 54 via conduit 60 and is passed to reverse osmosis zone 62. If desired, the aqueous phase from the extraction zone may be passed via an intermediate stripping zone (not shown) to substantially remove any entrained organic solvent.

The aqueous phase exiting the extraction zone at a rate of e.g., 1000 gallons per minute (gpm) and having a concentration of about 0.4N sodium chloride along with about 0.5 to 1 percent by weight organic components is then fed to reverse osmosis zone at a driving pressure of about 1000 psig. Reverse osmosis zone 62 has about 35,000 square feet of membrane area of a commercially available thin-film composite membrane. The retentate stream from the reverse osmosis zone having a volume of about 330 gpm and containing substantially all of the inorganic and organic chlorides present in the aqueous phase feed, is removed via conduit 64. This now concentrated stream requires substantially less energy when subjected to further treatment prior to disposal. The permeate stream comprising about 670 gpm flow and containing less than about 3000 ppm of inorganic chlorides and less than about 2000 ppm organic chlorides is recycled via conduit 66 to the first stage of the reaction zone, thereby substantially reducing the amount of fresh water required to be fed to the process via conduit 10.

What is claimed is:

1. In a continuous process for the production of an organic solvent solution of dichlorohydrin, the method for reducing the quantity of fresh water used in the reaction, which method comprises:
   (a) reacting allyl chloride, water and chlorine in a reaction zone to form an aqueous mixture of dichlorohydrin,
   (b) contacting in an extraction zone the reaction zone effluent with a water immiscible inert organic solvent for the dichlorohydrin to obtain a dichlorohydrin-enriched solvent and an aqueous phase,
   (c) passing said dichlorohydrin-enriched solvent from said extraction zone,
   (d) passing said aqueous phase from the extraction zone to a reverse osmosis zone,
   (e) subjecting said aqueous phase to reverse osmosis in said reverse osmosis zone to obtain: (1) a retentate stream having chloride content higher than said aqueous phase, and (2) a permeate stream having chloride content lower than said aqueous phase,
   (f) withdrawing said retentate stream, and
   (g) recycling at least part of said permeate stream from step (e) to the reaction zone of step (a).

2. A process as in claim 1 wherein step (c) the solvent is selected from at least one of an ester, aliphatic alcohol and aliphatic ketone containing from about 4 to about 18 carbon atoms.

3. A process as in claim 1 wherein the solvent is at least one of a saturated aliphatic ether and a chlorinated hydrocarbon containing up to 9 carbon atoms.

4. A process as in claim 1 wherein step (d) the aqueous phase contains from about 0.1 to about 0.6N of sodium chloride.

5. A process as in claim 1 wherein step (g) the amount of permeate recycled to the reaction zone is from about 10 to about 90% v of the water fed to the reaction zone.

6. A process as in claim 1 wherein the temperature of the reaction zone is controlled by controlling the temperature of the inert organic solvent entering the extraction zone.

7. A process as in claim 1 wherein intermediate to steps a and b, the reaction mixture is partially neutralized to a pH in the range from about 3.0 to about 6.5.

* * * * *